United States Patent [19]

Langerman

[11] Patent Number: 5,366,501
[45] Date of Patent: Nov. 22, 1994

[54] INTRAOCULAR LENS WITH DUAL 360 DEGREE HAPTICS

[76] Inventor: David W. Langerman, 99 Dutch Hill Plz., Orangeburg, N.Y. 10962

[21] Appl. No.: 60,636

[22] Filed: May 12, 1993

[51] Int. Cl.⁵ .............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,092,743 | 6/1978 | Kelman | 623/6 |
| 4,174,543 | 11/1979 | Kelman | 623/6 |
| 4,244,060 | 1/1981 | Hoffer | 623/6 |
| 4,402,579 | 9/1983 | Poler | 351/160 R |
| 4,439,873 | 4/1984 | Poler | 623/6 |
| 4,556,998 | 12/1985 | Siepser | 623/6 |
| 4,562,600 | 1/1986 | Ginsberg et al. | 623/6 |
| 4,573,998 | 3/1986 | Mazzocco | 623/6 |
| 4,608,049 | 8/1986 | Kelman | 623/6 |
| 4,681,585 | 7/1987 | Sayano et al. | 623/6 |
| 4,704,123 | 11/1987 | Smith | 623/6 |
| 4,795,460 | 1/1989 | Anis | 623/6 |
| 4,806,382 | 2/1989 | Goldberg et al. | 623/6 X |
| 4,863,463 | 9/1989 | Tjan | 623/6 |
| 5,108,429 | 4/1992 | Wiley | 623/6 |
| 5,180,390 | 1/1993 | Drews | 623/6 |

FOREIGN PATENT DOCUMENTS 2081469 2/1982 United Kingdom .

OTHER PUBLICATIONS

"CHIP" Posterior Chamber Lens, Investigational Device Specification.
Sheet (date unknown) by Domilens, Inc., Laguna Hills, Calif.

*Primary Examiner*—Randall L. Green
*Assistant Examiner*—Mary Beth Jones
*Attorney, Agent, or Firm*—Norbert P. Holler

[57] ABSTRACT

A posterior chamber intraocular lens (IOL) designed for in-the-bag implantation has a central optic and a surrounding pair of 360° haptics constituted by two concentric endless rings of different diameters. The outer diameter of the outer ring is slightly larger than the inner diameter of the capsular bag at the equator thereof, and the plane of the outer ring is anteriorly offset relative to the plane of the inner ring. When the IOL is properly implanted, the outer ring presses against the interior surface of the equatorial region of the capsular bag without unfurling the anterior capsular flap and constitutes a primary mechanical barrier to the migration of epithelial cells from the equatorial region into the optic region of the posterior capsule, while the inner ring presses against the anterior surface of the posterior capsule a short distance away from the equatorial region and constitutes a secondary mechanical barrier to the migration of epithelial cells which may not have been blocked by the primary barrier, thereby to inhibit capsular fibrosis and posterior capsular opacification. The haptics also serve to maintain the posterior capsule flush and taut against the optic, thereby to inhibit the formation of Elschnig's pearls on the posterior capsule.

9 Claims, 3 Drawing Sheets

FIG. 5
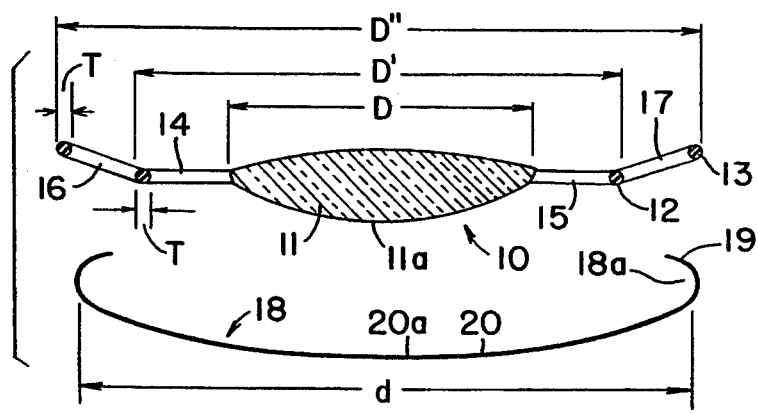
FIG. 6
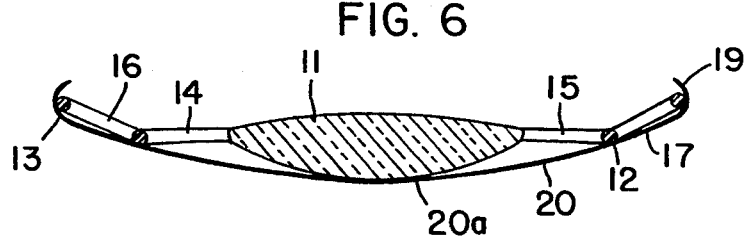
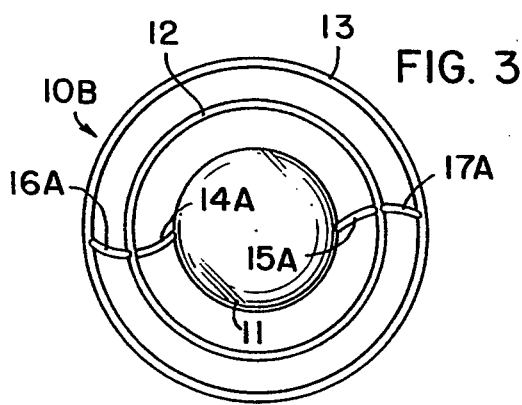
FIG. 3
FIG. 4
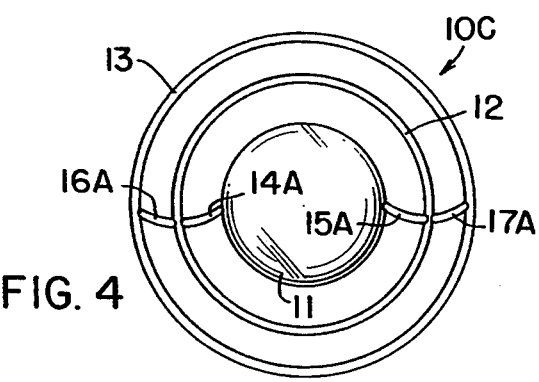

INTRAOCULAR LENS WITH DUAL 360 DEGREE HAPTICS

This invention relates to posterior chamber intraocular lenses, and in particular to such lenses which are designed for in-the-bag implantation, i.e., implantation in the residual capsular bag of an eye, following an extracapsular cataract extraction.

BACKGROUND OF THE INVENTION

Human beings, especially elderly persons, frequently tend to lose vision due to a gradually increasing clouding of the natural lens of the eye, which results from the development of a degree of opacity or clouding of the fibers (the cortex) surrounding the inert nucleus of the natural lens within the capsular bag housing the same. The condition where this opacity spreads into the center of the lens in the region behind the pupil so as to impair vision, is designated cataract. When the opacity has progressed sufficiently to cause the loss of useful functional vision, the cataract is said to be mature, and the only currently available treatment for that condition is the removal of the cataract by extraction of the lens from the eye and the replacement of the natural lens by an artificial lens. Such a cataract removal, which is probably one of the most common and widely performed ophthalmic surgical procedures these days, may involve either an intracapsular or an extracapsular extraction of the natural lens.

In an intracapsular cataract extraction (ICCE), the entire lens, including the nucleus, the cortex (the fibers) and the enveloping capsular bag, is taken out as a unit, with the zonular fibers which connect the bag to the ciliary body being first dissolved and the cataract then being removed with the aid of a suitable tool such as a low temperature probe (cryoadhesion) or an erysiphake. In such a case, the removal procedure is usually followed by the implantation of an intraocular lens (IOL) into the anterior chamber of the eye, with the lateral position fixation elements or haptics of the IOL (resilient loops, arms, or the like) being received in the angle of the anterior chamber (the angle is the groove or channel defined between the cornea in the limbal region thereof and the outer periphery of the iris where it joins the choroid coat). As an alternative, it has also been proposed to implant the IOL in the posterior chamber, with the haptics being received in the ciliary sulcus (the groove or channel defined at the juncture between the iris and the ciliary body), but this is always subject to the provision that steps are taken to ensure that the IOL does not come loose and fall into the vitreous humor.

In an extracapsular cataract extraction (ECCE), by way of contrast, first a major portion of the anterior capsule is cut away, leaving in place only that residual part of the capsular bag which consists of the posterior capsule and the remaining annular anterior capsular flap, then the lens nucleus is extracted from the capsular bag by any well-known type of expression or by phacoemulsification, and finally the cortex is removed by irrigation and aspiration. In such a case, the removal procedure is usually followed by the implantation of an IOL into the posterior chamber of the eye, with the haptics then being seated either in the ciliary sulcus outside the residual capsular bag, so that the entire residual capsular bag isolates the IOL from the vitreous humor, or physically within the residual capsular bag at the equatorial region thereof where the anterior capsular flap adjoins the posterior capsule, so that only the posterior capsule of the residual capsular bag isolates the IOL from the vitreous humor.

Many designs of intraocular lenses have been developed over the past 30–40 years. Representative ones are shown in Kelman U.S. Pats. Nos. 4,092,743, 4,174,543 and 4,608,049; Hoffer U.S. Pat. No. 4,244,060; Poler U.S. Pat. No. 4,402,579; Ginsberg et al. U.S. Pat. No. 4,562,600; Mazzocco U.S. Pat. No. 4,573,998; Sayano et al. U.S. Pat. No. 4,681,585; Smith U.S. Pat. No. 4,704,123; Anis U.S. Pat. No. 4,795,460; Goldberg et al. U.S. Pat. No. 4,806,382; and Choyce U.K. Pat. No. 2,081,469. Irrespective, however, of whether anterior chamber implantation or posterior chamber implantation or both has been the goal (posterior chamber implantation is by far the currently favored method), much of the emphasis in the development of intraocular lens designs has been on the forms and physical properties of the haptics, especially with regard to achieving an optimum haptic strength and flexibility, on the one hand so as to enable the optic to be implanted easily through a scleral, limbal or corneal incision and in a properly centered position in the eye, and on the other hand so as to ensure that the IOL is firmly seated in the eye secure against both dislodgement and rotation.

In addition to the IOL constructions proposed by the above-mentioned patents, Siepser U.S. Pat. No. 4,556,998 proposed a hydratable IOL which can be made in the form of a dehydrated solid body very small in size (e.g., 2–4 mm in diameter) and either having or being devoid of haptics. Following an extracapsular cataract extraction, the lens body, while still in its dehydrated state, is implanted in the residual capsular bag through a minimal size (e.g., 3 mm) corneal, scleral or limbal incision and is there hydrated by the natural fluid of the eye (the aqueous humor) and caused to swell to its desired size and optic power. The design of this IOL was aimed at achieving a proper positioning of the IOL and avoiding the exertion of undue pressure on the surrounding eye tissues.

To the extent necessary for an understanding of the present invention, therefore, the disclosures of these patents are incorporated herein in full by this reference.

While posterior chamber IOLs have proven to be of great benefit to persons who have undergone an ECCE, some post-operative complications do occasionally arise in connection therewith. One such complication is a post-implantation clouding of the posterior capsule which is a consequence of the fact that some epithelial cells are almost invariably left in the equatorial region of the capsular bag and not removed therefrom during the irrigation and aspiration phase after the surgeon has extracted the cataract. These cells have a tendency to migrate over the anterior surface of the posterior capsule toward the center or optic region thereof and, upon accumulating there, lead to capsular fibrosis and the formation of Elschnig's pearls, which in turn causes opacification of the posterior capsule and ultimately impairs vision in the same manner as the original cataract did, namely, by blocking the passage of light through the capsule to the retina. To remedy this situation, a further surgical procedure then becomes necessary, which may involve scraping and cleaning the accumulated fibers from the anterior surface of the posterior capsule behind the implanted IOL and possibly even a cutting out of the opacified region of the posterior capsule by means of a laser capsulotomy (which of late has substantially supplanted knife discission as the standard operating procedure). In any event, the possibility that the patient may be traumatized or even develop retinal detachment by such a procedure, coming after the patient has already gone through two losses of vision and one or two surgical procedures (the ECCE and the IOL implantation), is a prospect to be avoided.

The problems of capsular fibrosis and formation of Elschnig's pearls and of the resultant opacification of the posterior capsule following an ECCE have been recognized in the technical and patent literature; see, for example, the discussions thereof in the aforementioned U.S. Pats. Nos. 4,244,060 (Hoffer) and 4,562,600 (Ginsberg et al.). However, neither the ridged Hoffer lens nor the flanged Ginsberg lens described in those patents has been successful in eliminating these problems, in essence for the reason that in each of these lens designs one or more recesses are formed in the ridge or flange which projects posteriorly from the lens optic and is in contact with the front or anterior surface of the posterior capsule once the IOL has been implanted. Hoffer taught that such recesses (which are designated by reference numeral 34 in U.S. Pat. No. 4,244,060) are useful because they facilitate performance of a knife discission of a clouded posterior capsule without necessitating a dislodgement of the IOL. Ginsberg et al. taught that such recesses (which are designated by reference numerals 34 and 36 in U.S. Pat. No. 4,562,600) are useful because they facilitate rotational positioning of the IOL during the initial implant surgery and also minimize the post-implantation occurrence of unwanted and disturbing light reflections into the visual field. However, such recesses constitute breaches or gaps in the ridge or flange element of the lens which actually permit that which the ridge or flange of the lens is nominally intended to inhibit, namely, the migration of the epithelial cells into the optic region of the posterior capsule from the equatorial region of the capsular bag. The Hoffer patent evidences no awareness of this problem at all and thus offers no solution therefor whatsoever, while the Ginsberg et al. patent, though recognizing the possibility of cell migration through the notch-like recesses in the lens flange, suggests only the substitution of somewhat smaller indentations or of round holes for the notches, which still leaves one or more gaps in the flange through which cells can migrate.

In both the Hoffer and Ginsberg lenses, furthermore, the ability of the epithelial cells to migrate from the equatorial region of the capsular bag toward the optic region of the posterior capsule is not inhibited in any way until the cells are practically in the optic region, i.e., when they reach the zone of contact of the ridge or flange with the posterior capsule. In the Hoffer lens, on the one hand, this is so because the hairs constituting the haptic structure of the lens, though they are received in the cleft or fornix of the capsular bag, do not exert mechanical pressure on the entire interior surface of the equatorial region of the bag. Thus, not only are there many locations where the cells are not killed by mechanical pressure, but the Hoffer lens actually relies of the presence of the cells and the resultant fibrosis to anchor the IOL in the capsular bag. At the same time, the haptic structure, by virtue of the very nature of the hairs, cannot ensure that the rim portions and the ridge of the lens are pressed against the posterior capsule to block the migration of the epithelial cells into, and hence the propagation of capsular fibrosis and the formation of Elschnig's pearls in, the optic region of the posterior capsule. In the Ginsberg lens, on the other hand, the haptics cannot even partially inhibit cell migration because they are seated in the ciliary sulcus outside the capsular bag, while at the same time they cannot fully ensure adequate pressure contact between the flange of the IOL and the posterior capsule, so that again capsular fibrosis and pearl formation are not inhibited. Moreover, by virtue of the fact that in both the Hoffer lens and the Ginsberg lens there is an open space defined between the posterior capsule and the rear or posterior face of the optic, pearl formation in the optic region of the posterior capsule is not only not inhibited but is actually promoted. Of course, even were the haptics of the Ginsberg lens seated in the capsular bag, they would still not serve to block cell migration over the entire circumferential extent of the equatorial region of the bag.

In this connection it has also been shown that the use of haptics of the type (J, C and like-shaped arms or loops) shown in the Ginsberg patent, which are generally made appreciably longer, viewed diametrally of the optic, than the diameter of the capsular bag in the equatorial region thereof, entails certain drawbacks.

On the one hand, when such a lens is being implanted, the surgeon generally first seats one haptic, e.g., the inferior or lower haptic, in the equatorial region of the bag, e.g., at the 6 o'clock position, behind the proximate portion of the anterior capsular flap and then deflects the superior or upper haptic downwardly a bit (i.e., toward the optic) in an attempt to move it past the edge of the flap toward the posterior capsule before releasing the haptic to permit it to snap back to its full height in the equatorial region of the bag, e.g., at the 12 o'clock position. The risk in this procedure is that it may lead to the phenomenon of "capsular tuck" in which the deflected haptic, upon being released, does not clear the capsular flap but instead catches it and in effect tucks it back against the front face of the posterior capsule, by virtue of which the possibility of migration of epithelial cells from the equatorial region of the bag onto the optic region of the posterior capsule is enhanced.

On the other hand, since the length of these haptics exceeds the bag diameter, they can exert relatively high stresses on the equatorial region of the bag. The haptics, therefore, even if they do not tear through the capsular tissue in the equatorial region (which is always a risk, especially if the equatorial region has been weakened somewhat or even perforated during the surgical extraction of the cataract), can cause the anterior capsular flap to "unfurl," i.e., to be displaced radially outwardly of the posterior capsule. Such unfurling brings a portion of the equatorial region of the anterior capsular flap into substantially coplanar alignment with the posterior capsule and hence provides an even better access for cellular migration and proliferation onto the optic region of the posterior capsule.

The aforementioned U.S. Pat. No 4,795,460 (Anis) proposed an intraocular posterior chamber lens which, for the purposes of ease of implantation and secureness of positioning, has a pair of identically sized and shaped 2-ended haptic loop members disposed in parallel planes and extending in opposite directions each around somewhat more than one half (180° +) of the perimeter of the optic, the two ends of one member being secured to the optic substantially tangentially thereof at the 3 o'clock position and the ends of the other member being correspondingly secured to the optic at the 9 o'clock position. The loop members are stated as defining a generally continuous circular periphery adapted to engage the periphery of the capsular bag over substantially 360°, by virtue of which the IOL assertedly can be implanted in any position and is secured against inadvertent dislodgement. The patent is entirely silent, however, on the problem of post-implantation posterior capsular fibrosis, pearl formation and opacification and expresses no awareness of the problem of unfurling of the anterior capsular flap and its contribution to posterior capsular opacification. In point of fact, the location of the loop members in two adjacent planes and their joint generally single-diameter locus does not afford an adequate barrier to epithelial cell migration.

BRIEF DESCRIPTION OF THE INVENTION

It is an object of the present invention to provide a novel and improved intraocular lens construction by means of which the aforesaid drawbacks and disadvantages of the known IOLs can be effectively overcome.

A more specific object of the present invention is the provision of such an IOL construction, which is characterized by a dual full 360° haptic structure that extends entirely around the perimeter of the optic of the lens and constitutes a circumferentially uninterrupted and unitary barrier arrangement at each of two diametrally spaced locations in relatively close proximity to the equatorial region of the capsular bag for blocking cell migration over the posterior capsule, and which at the same time is so dimensioned and has such physical properties as to not only enable the IOL to be implanted through a minimal size scleral, limbal or corneal incision but as to also enable the haptic structure to be properly implanted and firmly seated within the capsular bag without risking the occurrence of capsular tuck, without overstressing the equatorial region of the bag, and without engendering an unfurling of the anterior capsular flap of the bag.

Generally speaking, the objectives of the present invention are achieved by an IOL which is adapted for in-the-bag implantation following an ECCE and includes a pair of full 360° haptics constituted by two resiliently flexible, concentric, closed and continuous planar rings about 0.2 mm thick, having different diameters and extending around the entire perimeter of the optic of the lens. The smaller ring is connected to the peripheral edge of the optic by a first pair of bridging elements extending generally diametrally of the smaller ring, and the larger ring is connected to the smaller ring by a second pair of bridging elements extending generally diametrally of the larger ring, with all the bridging elements preferably being located in the same diametral region of the IOL. The two rings are disposed in separate planes, with the plane of the larger ring being anteriorly offset somewhat from the plane of the smaller ring, and the diameter of the larger ring at its outer periphery is somewhat, albeit only slightly, e.g., between about 0.5 mm and about 1.5 mm, larger than the interior diameter of the capsular bag in the equatorial region of the latter.

The entire lens, including the optic, the haptics and the bridging elements, may be formed as one piece of the same material by any suitable technique, such as injection molding, lathe cutting, or the like. However, some or all of the lens components may be formed separately, if desired of different materials, and then connected and secured to each other. Also, the bridging elements, which are of thin rod-shaped configuration, the thickness (diameter) of which is essentially the same as that of the haptics, i.e., about 0.2 mm, may be either straight or slightly arcuate elements, with each outer bridging element on one side of the optic being substantially continuous with the associated inner bridging element on the same side of the optic. Where the bridging elements are arcuate, the direction of the curvature of the two elements on one side of the optic may be in the same sense as or in the opposite sense to the direction of the curvature of the two elements on the other side of the optic.

The IOLs according to the present invention may be made entirely of any suitable biocompatible material, for example, polymethylmethacrylate (PMMA), silicone, collagen, hydrogel, and the like, and in addition the haptics and the rods or bridging elements therefor may also be made of polypropylene (prolene). The optic of the lens, which may be symmetrically or asymmetrically biconvex or may be planoconvex in either sense (i.e., with the convex portion thereof disposed either posteriorly or anteriorly thereof), will preferably be of circular configuration having a diameter between about 4 mm and about 8 mm, although the optic may be of oval or elliptical configuration with a major diameter between about 5 mm and about 8 mm and a minor diameter between about 3.5 mm and about 6 mm. The haptics are of substantially circular configuration, with the outer ring having an outer diameter which is, as already indicated, between about 0.5 mm and about 1.5 mm greater than the inner diameter of the capsular bag, and with the inner ring having an outer diameter about 2 mm smaller than that of the outer ring.

The advantages accruing from these structural characteristics will be readily comprehended. One is that, for the purpose of introducing the lens into the eye, the surgeon is able to grip the haptics at the opposite sides of the lens, i.e., at the 3 o'clock and 9 o'clock positions (considering the bridging elements as being located at the top and bottom of the lens, i.e., at the 12 o'clock and 6 o'clock positions), and to press them inwardly toward and against the peripheral edge of the optic. Thus, although the dimension of the lens in the diametral region thereof where the bridging elements are located remains essentially unchanged at its nominal value, the side to side dimension of the lens is effectively reduced to the transverse diameter of the optic (which would be the minor diameter in the case of an oval optic) or even to about one-half that diameter if the optic is made of a soft material and can be folded in half for the insertion, so that the corneal, limbal or scleral incision through which the lens is inserted into the eye need only be made (depending on how the lens is inserted) just slightly larger than the either full or reduced side to side dimension of the optic.

Another advantage is that once the IOL has been properly implanted into the residual capsular bag of the eye and the haptics have reverted to their full circular configuration, which in the case of the outer or larger ring means to a diameter adapted to and just slightly greater than the equatorial diameter of the capsular bag, the larger ring presses along its entire circumference against the interior surface of the residual capsular bag in the equatorial region thereof without overstressing the latter and without engendering an unfurling of the anterior capsular flap. At the same time, by virtue of the anterior offset of the larger outer ring relative to the smaller inner ring, the latter presses along its entire circumference against the anterior surface of the posterior capsule a short distance radially inwardly of the equatorial region. The larger ring thereby constitutes a primary mechanical barrier for inhibiting migration of epithelial cells from the equatorial region onto the posterior capsule and toward the optic region thereof, while the smaller ring constitutes a secondary mechanical barrier for inhibiting migration, over the posterior capsule and toward the optic region thereof, of epithelial cells that were not blocked by the larger ring. Concomitantly therewith, the optic region of the posterior capsule is maintained taut against the posterior surface of the optic for inhibiting formation of Elschnig's pearls in the optic region of the posterior capsule.

BRIEF DESCRIPTION OF THE DRAWING

The foregoing and other objects, characteristics and advantages of the present invention will be more fully understood from the following detailed description of various embodiments thereof when read in conjunction with the accompanying drawings, in which:

FIG. 3 is a plan view of an IOL similar to that shown in FIG. 1 but provided with arcuate bridging elements for the haptics according to a modified form of the invention;

FIG. 4 is a view similar to FIG. 3 but shows the IOL as having arcuate bridging elements for the haptic according to another modified form of the invention;

FIG. 5 is an exploded transverse sectional view diagrammatically showing an IOL with an asymmetrically biconvex optic prior to its insertion into the residual capsular bag of an eye;

FIG. 6 is a transverse sectional view showing the IOL as in FIG. 5 after its insertion into the capsular bag;

DETAILED DESCRIPTION OF THE INVENTION

Figure 1:
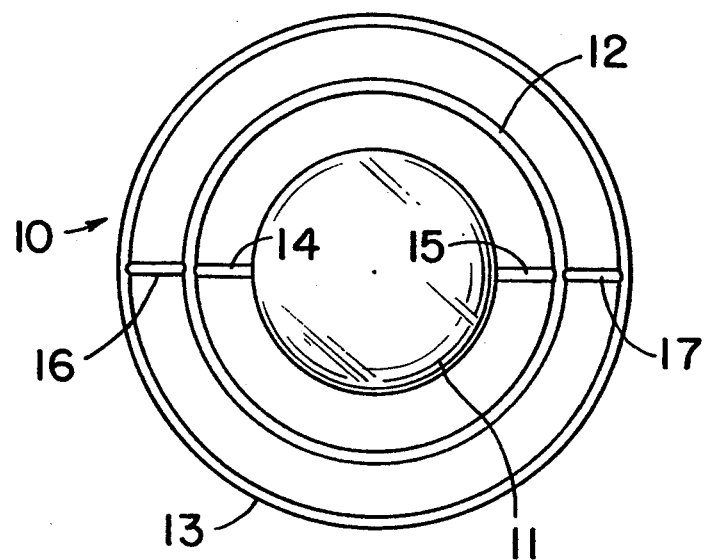
FIG. 1 is a plan view of an intraocular lens according to one embodiment of the present invention, the lens being shown as including a circular optic and straight bridging elements for the haptics.

Referring now to the drawing in greater detail and in particular to FIG. 1, an intraocular lens 10 according to one embodiment of the present invention is there shown which includes an optic 11 of circular configuration having a diameter D (see FIG. 5) and a dual haptic structure consisting of a pair of closed and continuous planar rings 12 and 13 of likewise circular configuration but of different outer diameters D' and D'', of which the diameter D'' is just slightly larger than the inner diameter d of the equatorial region or zone 18a of the residual capsular bag 18 into which the lens 10 is to be inserted as shown in FIGS. 5 and 6. The rings 12 and 13, which have a thickness T and are resiliently flexible, are arranged concentrically with each other and the optic and extend around the entire perimeter of the optic, with the plane of the larger outer ring 13 being anteriorly offset somewhat relative to the plane of the smaller inner ring 12. The two rings and the optic are interconnected with each other by means of respective pairs of straight rod-like bridging elements 14, 15 between the inner ring and the optic and 16, 17 between the outer and inner rings, with all the bridging elements, which have the same thickness as the rings, being arranged in a common diametral plane of the IOL.

It should be noted that the above-stated relationship between the outer diameter D'' of the lens 10 and the inner diameter d of the capsular bag 18 is of great significance in the present invention. The equatorial zone diameter of a capsular bag in the eye of a human being varies, of course, as is well known and as is to be expected, from one person to another. In general, as far as I am aware, conventional practice among ophthalmologists has been and still is to implant in a given patient an IOL having a "length" (the maximum distance, measured diametrally of the optic, between the arched seating portions of the loops or haptics) which is up to about 3.5 mm greater than the equatorial zone diameter of the capsular bag of that patient, for the express purpose of achieving a secure seating of the IOL in the bag. Experience has shown, however, that the haptics of such lenses exert a radial pressure on the equatorial region of the bag which can cause the anterior capsular flap 19 to be literally unfolded or unfurled with a consequent shifting of the equatorial zone of the bag in a posterior direction. Moreover, where as a result of the ECCE the anterior capsular flap is very narrow and/or the equatorial zone is defective or torn, or where the IOL is "dialed" or rotated about its axis during the insertion thereof into the bag, the likelihood of the haptics completely unfurling the anterior capsular flap is actually enhanced. As previously mentioned, such unfurling aids the migration of epithelial cells from the equatorial region of the bag onto the posterior capsule 20 and thus the subsequent initiation of capsular fibrosis and posterior capsular opacification. As has also been previously mentioned, the use of the IOLs with arched "J" haptics also entails the risk of a capsular tuck occurring during the implantation procedure, which likewise promotes cell migration and proliferation onto the posterior capsule and the resultant posterior capsular fibrosis and opacification.

In order to avoid these drawbacks, the present invention contemplates, as an essential aspect thereof, a proper diametral dimensioning of the outer ring 13 of the haptic structure of the lens 10 relative to the size of the capsular bag. In particular, it is contemplated that the outer diameter D'' of the ring 13 should be about 0.5 mm to about 1.5 mm greater than the inner diameter d of the equatorial zone of the capsular bag 18. Thus, when the IOL has been properly implanted, the ring 13 will apply some radially outward pressure on the equatorial zone of the bag, not enough to cause the undesired unfurling but sufficient to kill any epithelial cells it engages. Moreover, by virtue of its uninterrupted circular form, the ring 13 applies such pressure along the entire 360° circumference thereof against the equatorial zone of the capsular bag over its full circumferential extent. The ring 13 thus constitutes a mechanical barrier against migration of those epithelial cells which it contacts onto the posterior capsule and toward the optic region thereof.

At the same time it must be appreciated, however, that the width of the equatorial zone of the capsular bag is considerably greater than the region of contact between it and the ring 13 (the thickness of the latter is only about 0.2 mm). As a consequence thereof it is entirely possible that there may be some epithelial cells present in the radially outermost circumferential region of the posterior capsule adjacent the equatorial zone, which not only were not removed by the surgeon during the irrigation and aspiration procedure but then were not contacted and blocked by the outer ring 13 of the haptic structure of the implanted lens. It is to compensate for this possibility that the inner ring 12 is provided as a part of the haptic structure and that the plane of the outer ring 13 is anteriorly offset relative to the plane of the inner ring. The magnitude of the offset is determined by the bridging elements 16 and 17 being anteriorly inclined at an angle of about 15° to the plane of the optic, although the angle may be even somewhat smaller (e.g., as little as 10°) or somewhat larger (e.g., as great as 30°).

By virtue of this arrangement, the constraining force exerted on the haptic structure of the implanted IOL by the capsular bag at the outer ring 13 is transmitted via the bridging elements 16 and 17 to the inner ring 12 and has the effect of slightly displacing the latter in a posterior direction relative to both the optic and the outer ring. The magnitude of this displacement need not be very great, and is determined by the bridging elements 14 and 15 ending up being posteriorly inclined at an angle of about 10° to the plane of the optic, as indicated in FIG. 6, although this angle may be as small as about 5° or as large as about 15°. As a result, with the inner ring being supported by the optic only via the pair of bridging elements 14 and 15, the inner ring is pressed against the posterior capsule a small distance, on the order of about 2 mm, radially inwardly of the equatorial zone (see FIG. 6) and thereby constitutes a secondary mechanical barrier to the migration, over the posterior capsule and toward the optic region thereof, of epithelial cells that were not blocked by the primary barrier, i.e., the outer ring. Concomitantly, the optic region 20a of the posterior capsule 20 is maintained flush and taut against the posterior face 11a of the optic 11, at least in the region of the optic axis, whereby the formation and growth of Elschnig's pearls on, and the consequent opacification of, the posterior capsule is inhibited.

Merely by way of example, if the capsular bag diameter of a patient is about 9.4 mm, the outer diameter D" of the outer ring 13 should be in the range of about 9.9 mm to about 10.9 mm, with the outer diameter D' of the inner ring 12 then being in the range of about 7.9 mm to about 8.9 mm. In conjunction therewith, the diameter D of the optic 11 may be in the range of about 4 mm to about 8 mm, although it will usually be at the middle of the range (e.g., about 6 mm) or even somewhat nearer the lower end of the range (e.g., about 5 mm).

It will further be understood that the structure of the IOL 10 as so far described greatly facilitates the implantation procedure and minimizes the trauma to the patient. Thus, for the purpose of inserting the lens into an eye, the surgeon can grip the lens with a pair of forceps at the opposite sides thereof, i.e., at the 3 o'clock and 9 o'clock positions (viewing the bridging elements as located at the 6 o'clock and 12 o'clock positions), and press the rings 12 and 13 inwardly toward the optic. This in effect reduces the width of the lens substantially to the width (the diameter) of the optic while the length of the lens measured in the direction of the bridging elements remains unchanged, which enables the lens to be passed through a corneal, scleral or limbal incision the size of which need be only slightly greater than the diameter of the optic. Moreover, the introduction of the lens into the capsular bag is greatly simplified because orientation of the IOL is no longer a matter of concern, so that the lens need not be dialed for proper positioning, and because the limited pressure of the outer haptic on the equatorial zone of the capsular bag is applied substantially uniformly along the entire circumferential extent of the equatorial zone, so that localized overstressing of the zone is likewise no longer a matter of concern.

Figure 2:
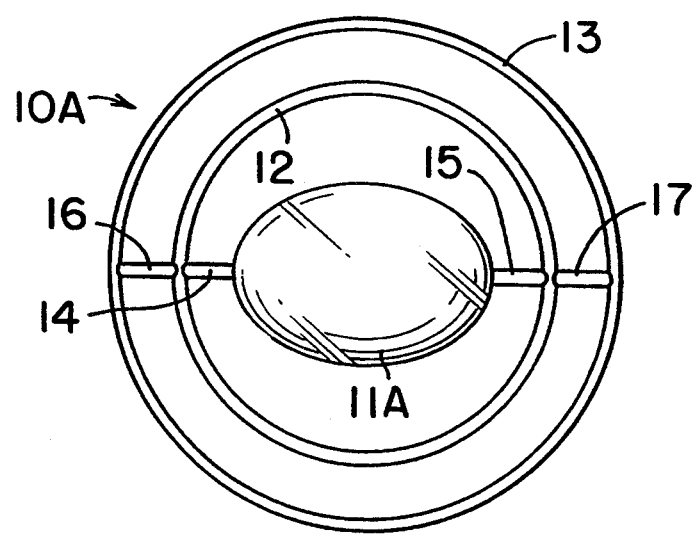
FIG. 2 is a similar view of an IOL including an oval optic.

The principles of the present invention can, of course, be embodied in IOL structures differing somewhat from that of the lens 10 shown in FIG. 1. For example, the lens 10A shown in FIG. 2 is substantially identical with the lens 10 but differs therefrom in that in lieu of the circular optic 11 it has an optic 11A which is of oval configuration. In such a lens, the optic would preferably have a major diameter in the range of about 5 mm to about 8 mm and a minor diameter in the range of about 3.5 mm to about 6 mm as a means for enabling the lens to be inserted endwise into the eye through an even smaller corneal, scleral or limbal incision than a comparable lens having a circular optic.

The lenses 10B and 10C shown in FIGS. 3 and 4, respectively, on the other hand, are also substantially identical with the lens 10 of FIG. 1, but here, though having circular optics 11, they differ from the lens 10 in that they utilize two pairs of bridging elements 14A, 15A and 16A, 17A which are arcuate rods rather than straight ones. As in the lens 10, of course, in each of the lenses 10B and 10C the two bridging elements 14A and 15A of the inner pair of elements extend generally diametrally of the inner ring 12, the two bridging elements 16A and 17A of the outer pair of elements extend generally diametrally of the outer ring 13, all four bridging elements are located in a common diametral region of the lens, and the two bridging elements 14A, 16A and 15A, 17A at each "end" of the lens are essentially continuations of each other. The difference between the lenses 10B and 10C is that, as viewed circumferentially of the lens in a clockwise sense, in the lens 10B the direction of the curvature of the two bridging elements 14A and 16A at one side of the lens is the same as the direction of the curvature of the bridging elements 15A and 17A at the opposite side of the lens (in other words, both concavities face in the clockwise direction), while in the lens 10C the direction of the curvature of the set of bridging elements 14A, 16A is opposite to that of the set of bridging elements 15A, 17A (in other words, one concavity faces in the clockwise direction while the other concavity faces in the counterclockwise direction). Here it should be noted, merely in passing, that the description of the curvatures could be reversed without any change in either FIG. 3 or FIG. 4 being required. Thus, it may be said that, as viewed along the axis of the IOL, the two directions of the curvatures of the bridging elements shown in FIG. 3 are opposite to each other (one concavity facing upwardly and the other downwardly) while the two directions of the curvatures of the bridging elements shown in FIG. 4 are the same (both concavities face upwardly—they could just as well face downwardly, of course, if the IOL 10C were rotated through 180° about its axis). However the arrangement is described, the structural design would be either that of FIG. 3 or that of FIG. 4, and in any such lens the purpose of the curvature of the bridging elements is to impart to the haptic structure a degree of flexibility in the 6 o'clock to 12 o'clock direction, which will permit compression and folding in that direction (rather than only perpendicular thereto) if the surgeon so desires.

It will be understood, of course, that as further variants of the invention, an IOL having an oval optic such as is shown in FIG. 2 may have a haptic structure utilizing arcuate bridging elements such as are shown in FIGS. 3 and 4.

Figure 7:
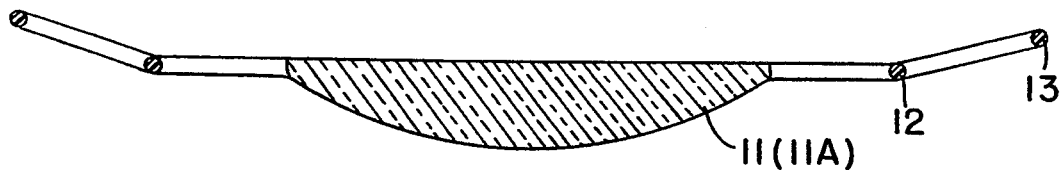
FIG. 7 is a transverse section through an IOL according to the present invention and shows the same as including a plano-convex optic with the convex face directed posteriorly of the lens.
Figure 8:
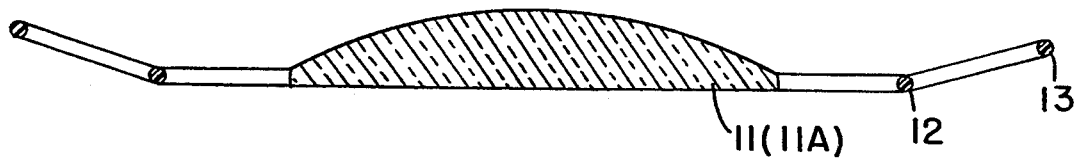
FIG. 8 is a view similar to FIG. 7 but shows an IOL having a plano-convex optic with the plane face directed posteriorly of the lens.
Figure 9:
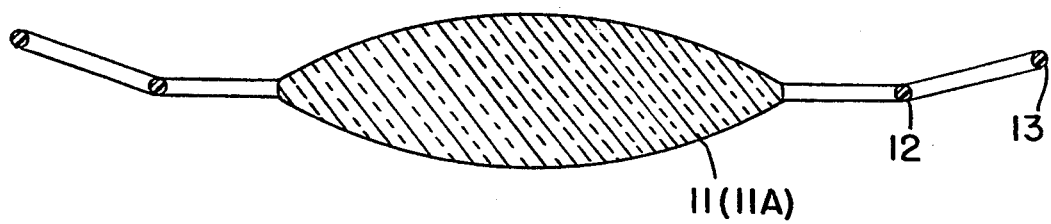
FIG. 9 is a view similar to FIGS. 7 and 8 but shows an IOL having a symmetrically biconvex optic.

It will further be understood that the optic of an IOL according to the present invention, irrespective of whether it is of circular or oval configuration and irrespective of whether the bridging elements of the associated haptic structure are straight or arcuate, may have a variety of cross-sectional shapes. Thus, either the optic 11 or the optic 11A may be asymmetrically biconvex as shown in FIGS. 5 and 6, or it may be plano-convex with its convexity directed posteriorly of the lens as shown in FIG. 7 or anteriorly of the lens as shown in FIG. 8, or it may be symmetrically biconvex as shown in FIG. 9. Also, in each given case the entire lens may be a one-piece structure made by injection molding, lathe-cutting or the like, or it may be assembled from a plurality of components which have been made either all of one material or of different materials selected, as deemed appropriate, from those referred to hereinabove.

It will be understood that the foregoing description of preferred embodiments of the present invention is for purposes of illustration only, and that the various structural and utilitarian features herein disclosed are susceptible to a number of modifications and changes none of which entails any departure from the spirit and scope of the present invention as defined in the hereto appended claims.

I claim:

1. A posterior chamber intraocular lens for implantation into an eye between the posterior capsule and the anterior capsular flap of the residual capsular bag that remains in the eye following an extracapsular cataract extraction, comprising:
   (a) an optic having anterior and posterior surfaces; and
   (b) a pair of haptics connected with said optic for positioning said optic properly in said residual capsular bag,
      (i) said haptics being constituted by two resiliently flexible, concentric, closed, planar rings having different diameters and extending around the entire perimeter of said optic,
      (ii) the smaller of said rings being connected to the peripheral edge of said optic by a first pair of bridging elements extending generally diametrally of said smaller ring,
      (iii) the larger of said rings being connected to said smaller ring by a second pair of bridging elements extending generally diametrally of said larger ring, with each of said first bridging elements being proximate to a respective one of said second bridging elements,
      (iv) the plane of said larger ring being parallel to but offset anteriorly from the plane of said smaller ring, and
      (v) the outer diameter of said larger ring at its outer periphery being slightly larger than the inner diameter of said residual capsular bag in the equatorial region thereof;
   (c) whereby, upon proper implantation of the lens into the eye,
      (i) said larger ring presses along its entire circumference against the interior surface of said residual capsular bag in the equatorial region thereof without overstressing the latter and without engendering an unfurling of said anterior capsular flap, said larger ring thereby constituting a primary mechanical barrier for inhibiting migration of epithelial cells from said equatorial region onto and toward the optic region of said posterior capsule of said residual capsular bag,
      (ii) said smaller ring presses along its entire circumference against the anterior surface of said posterior capsule a short distance radially inwardly of said equatorial region to constitute a secondary mechanical barrier for inhibiting migration, over said posterior capsule and toward said optic region thereof, of epithelial cells that were not blocked by said larger ring, and
      (iii) the optic region of said posterior capsule is maintained flush and taut against said posterior surface of said optic for inhibiting formation of Elschnig's pearls in the optic region of said posterior capsule.

2. An intraocular lens as claimed in claim 1, wherein all of said bridging elements are of rod-shaped configuration, and each bridging element of said first pair is substantially continuous with the proximate bridging element of said second pair.

3. An intraocular lens as claimed in claim 2, wherein all of said bridging elements are straight rods.

4. An intraocular lens as claimed in claim 2, wherein all of said bridging elements are arcuate rods, and the curvature of each bridging element of said first pair is in the same direction as the curvature of said proximate bridging element of said second pair.

5. An intraocular lens as claimed in claim 4, wherein the direction of the curvature of the proximate first and second bridging elements located at one side of said optic is opposite to the direction of the curvature of the proximate first and second bridging elements at the opposite side of said optic.

6. An intraocular lens as claimed in claim 4, wherein the direction of the curvature of the proximate first and second bridging elements at one side of said optic is the same as the direction of the curvature of the proximate first and second bridging elements at the opposite side of said optic.

7. An intraocular lens as claimed in claim 1, wherein the outer diameter of said larger ring is between about 0.5 mm and about 1.5 mm greater than the inner diameter of said residual capsular bag in the equatorial region thereof.

8. An intraocular lens as claimed in claim 1, wherein said optic is of circular configuration and has a diameter between about 4 mm and about 8 mm.

9. An intraocular lens as claimed in claim 1, wherein said optic is of oval configuration and has a major diameter between about 5 mm and about 8 mm and a minor diameter between about 3.5 mm and about 6 mm.

* * * * *